United States Patent [19]

Mulholland

[11] 4,029,089

[45] June 14, 1977

[54] PRONE STANDER

[76] Inventor: Lawrence K. Mulholland, 985 Ann Arbor, Ventura, Calif. 93003

[22] Filed: June 14, 1976

[21] Appl. No.: 695,767

[52] U.S. Cl. .............................. 128/80 R; 128/80 G

[51] Int. Cl.[2] .............................. A61F 3/00

[58] Field of Search ................. 128/80 R, 80 G, 83, 128/87 R, 84 R, 68; 297/4, 5, 6; 280/1, 219, 220

[56] References Cited

UNITED STATES PATENTS

| | | | |
|---|---|---|---|
| 2,210,269 | 8/1940 | Taylor | 128/80 R X |
| 3,249,368 | 5/1966 | Ginzburg | 128/84 R |
| 3,958,568 | 5/1976 | Gaddy | 128/80 R |

*Primary Examiner*—John D. Yasko

*Attorney, Agent, or Firm*—Robert E. Geauque

[57] ABSTRACT

A prone stander which is constructed of a main center post assembly which is inclineable to different positions with respect to a supporting base, the supporting base being mounted upon wheels. The user's feet are to be located upon a platform which is movable with respect to the center post assembly. There is a knee support, a hip support and a chest support mounted upon the center post assembly with the knee support and the chest support being adjustable in respect thereto. The knee support supports the knee both in the outward direction and in the inward direction. A tray can be attached to the prone stander.

15 Claims, 8 Drawing Figures

PRONE STANDER

BACKGROUND OF THE INVENTION

The device of this invention is designed in particular to be used as a rehabiliation device for cerebral palsy victims, these victims usually being children. However, it is considered to be within the scope of this invention that the device could be used as a rehabilitation piece of equipment for any persons which are not capable of standing independently upon their feet.

It is not uncommon for certain cerebral palsy victims to not be able to stand unaided. But if such persons do not stand, their bone and muscle structure become soft within their legs and hips and these people become increasingly worse. By using a prone stander the person is supported upon his feet and weight is supplied to the bones and muscles. It is this weight that faciliates the development of bone and muscle structure.

SUMMARY OF THE INVENTION

The prone stander of this invention is designed for use by individuals with central nervous system damage or dysfunction. It provides a means for achieving graduated weight bearing while the individual is in a prone (spacially oriented) position.

One objective of this invention is that the device is collapsible and therefore facilitates portability and also during use is capable of being moved since it is mounted on wheels.

A further objective of this invention is that it prevents adduction of the user's knees.

Another object of this invention is that it securely maintains and positions the user's legs and torso yet leaving the person's arms free for movement in a normal manner.

A still further objective of this invention is that it constructed of light-weight materials. Therefore, the overall device is light in weight.

A still further objective of this invention is that it is manufacturable at a relatively inexpensive price.

A still further objective of this invention is that the device is adjustable to accommodate children of heights from 32 inches to 55 inches.

A still further objective of this invention is that the device is highly mobile, extremely stable and does not require to be attached to any other fixed object.

The prone stander of this invention comprises a base assembly which is mounted upon wheels. Included within the base assembly is a brake assembly which can securely lock the wheels thereby locating the device in a fixed position to prevent undesirable movement of the device. A main center post is attached to the base assembly and is inclinable to different positions in respect thereto. Upon the center post is adjustably located a knee support unit and a chest support unit. Fixed to the center post is a hip support unit. Each of the support units are to prevent outward lateral movement of the person's torso and also inward lateral movement (or adduction) of the person's knees. Each of the support units include a pair of U-shaped rod members which are laterally adjustable with respect to the center post. Within each of the pair of members are located a pair of wide fabric straps which are to be used to bind the user of the device to the device. The user's feet are to be placed upon a supporting plate which is located upon the center post assembly adjacent the base assembly. This supporting plate is to be adjustable with respect to the center post assembly to accommodate different heights of users. A tray may be connected to the device, between the center post assembly and the base assembly and is to be positioned horizontal adjacent the user's hands and arms. The height of the tray is adjustable and moves with and stays horizontal no matter what the inclination of the center post assembly.

DETAILED DESCRIPTION OF THE SHOWN EMBODIMENT

Figure 1:
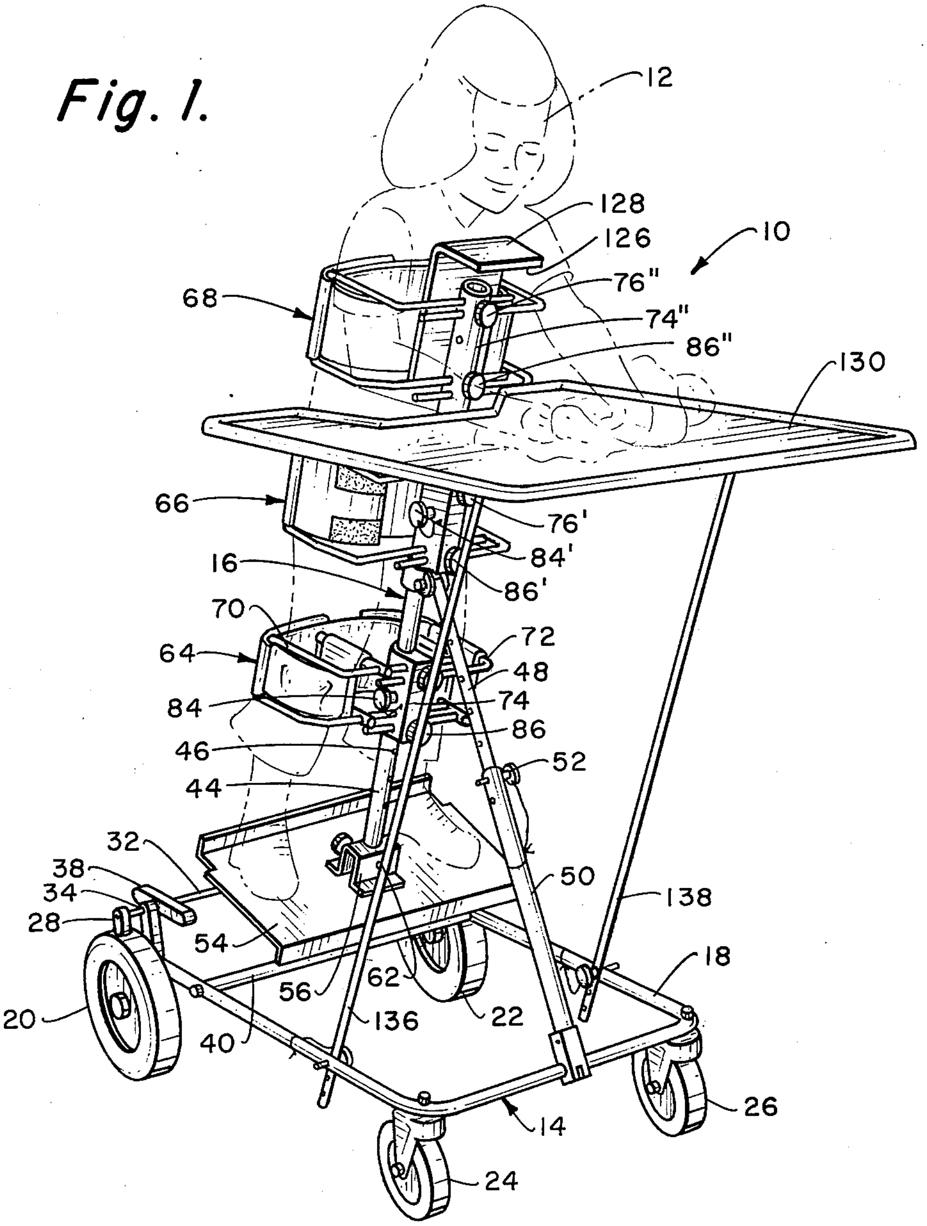
FIG. 1 is an isometric view of the prone stander of this invention showing in phantom lines a child strapped within the device.
Figure 5:
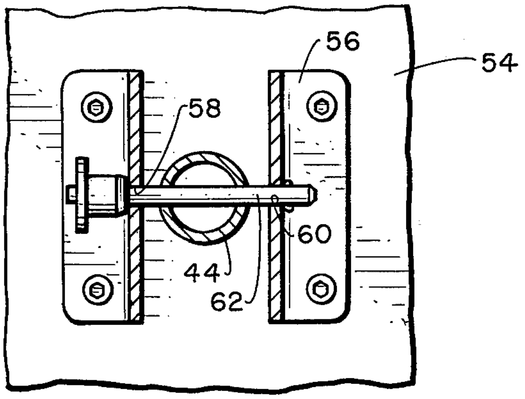
FIG. 5 is a cross-sectional view taken along line 5—5 of FIG. 2.

Referring particularly to the drawings, there is shown in FIG. 1 the prone stander 10 of this invention upon which is located a child 12. The prone stander 10 includes a base assembly 14 and a center post assembly 16.

The base assembly 14 is comprised of cylindrical tubular stock taking the form of a substantially rectangularly shaped main frame member 18. Rotatably supported upon the main frame member 18 are a pair of enlarged rear wheels 20 and 22 and a pair of smaller sized front wheels 24 and 26. Wheels 24 and 26 are castered upon the frame member 18.

The wheels 20 and 22 are capable of being contacted by brake members 28 and 30, respectively. The brake members 28 and 30 are both fixedly secured to an elongated rod 32. The rod 32 is rotatably mounted within a pair of upright members 34 and 36. The members 34 and 36 are secured to the main frme member 18. Also, support 34 functions to rotatably mount the wheel 20 with support 36 functioning to rotatably mount the wheel 22.

Figure 2:
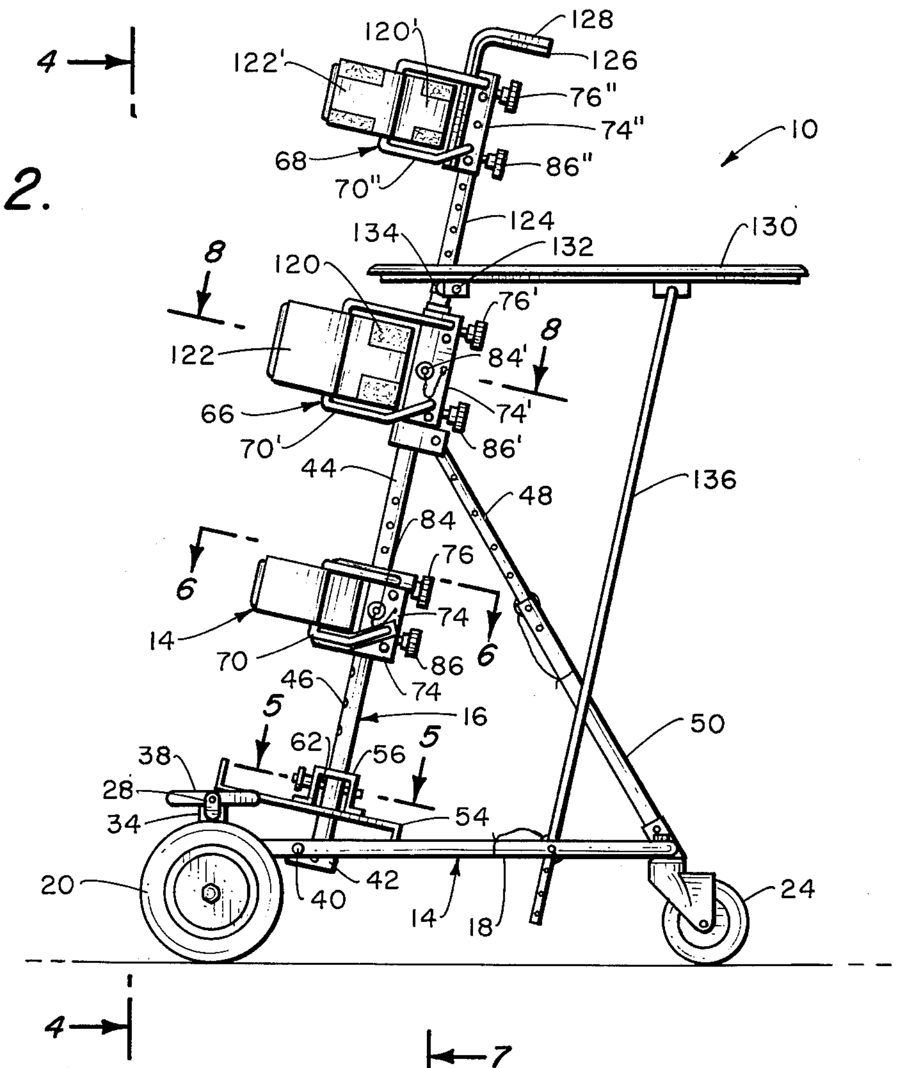
FIG. 2 is a side view of the prone stander of this invention showing the device in the position to accommodate a maximum height child.
Figure 6:
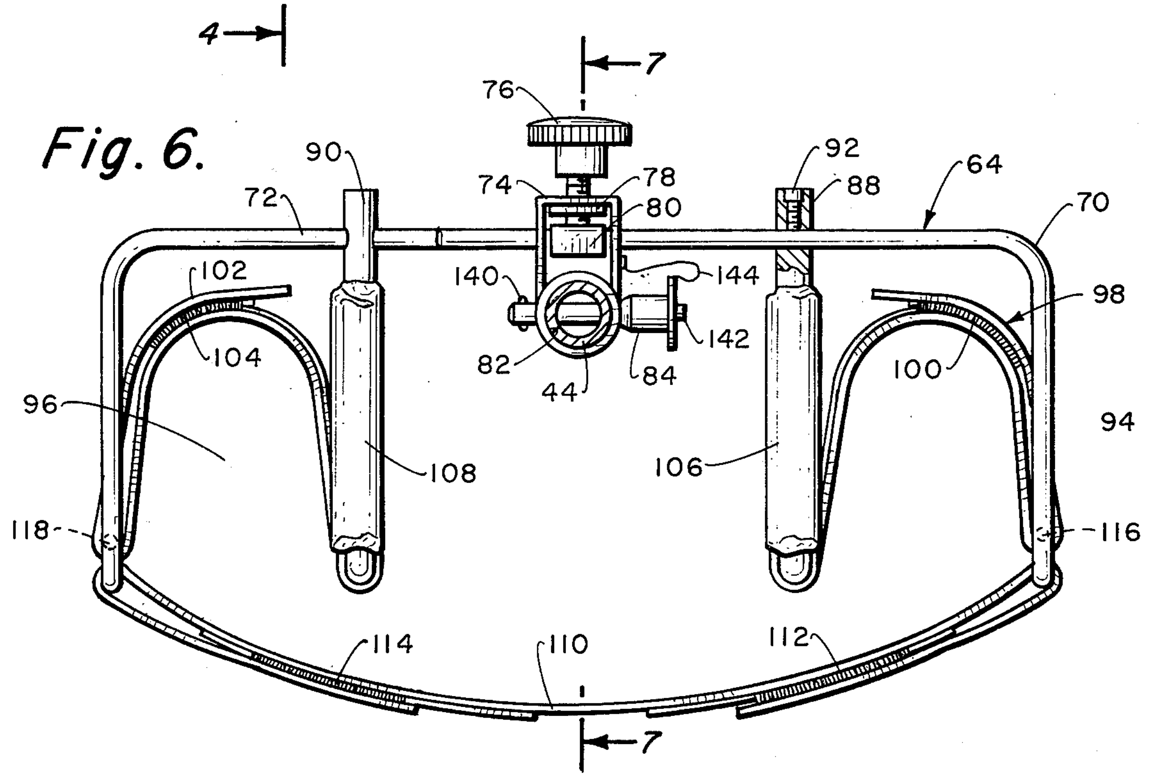
FIG. 6 is a partly in cross-section view showing in detail the knee support unit incorporated within the prone stander of this invention taken along line 6—6 of FIG. 2.
Figure 3:
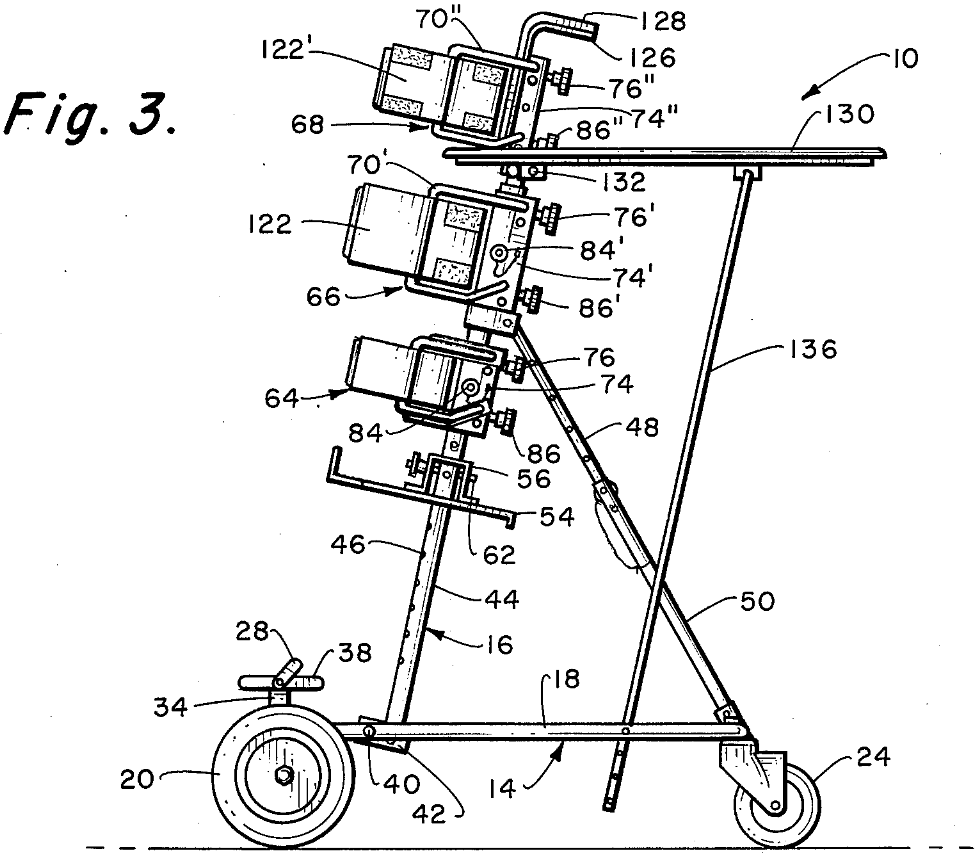
FIG. 3 is a view similar to FIG. 2 but showing the prone stander in a position to accommodate a minimum height child.
Figure 8:
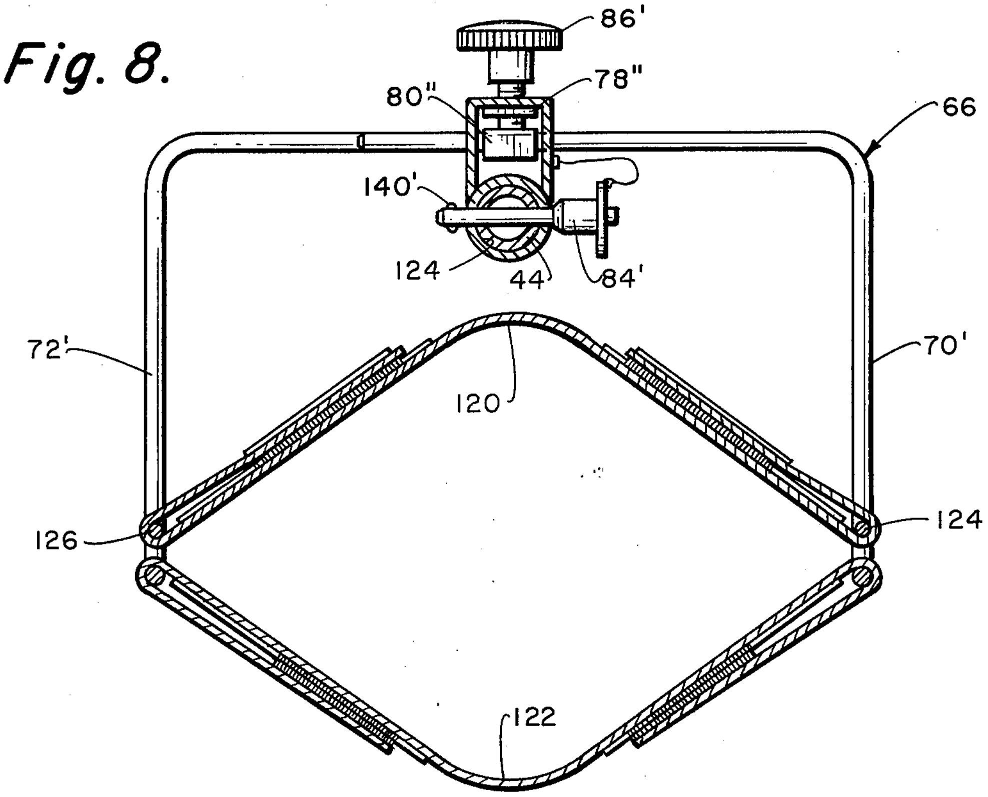
FIG. 8 is a cross-sectional view through the hip support unit incorporated within the prone stander of this invention.
Figure 4:
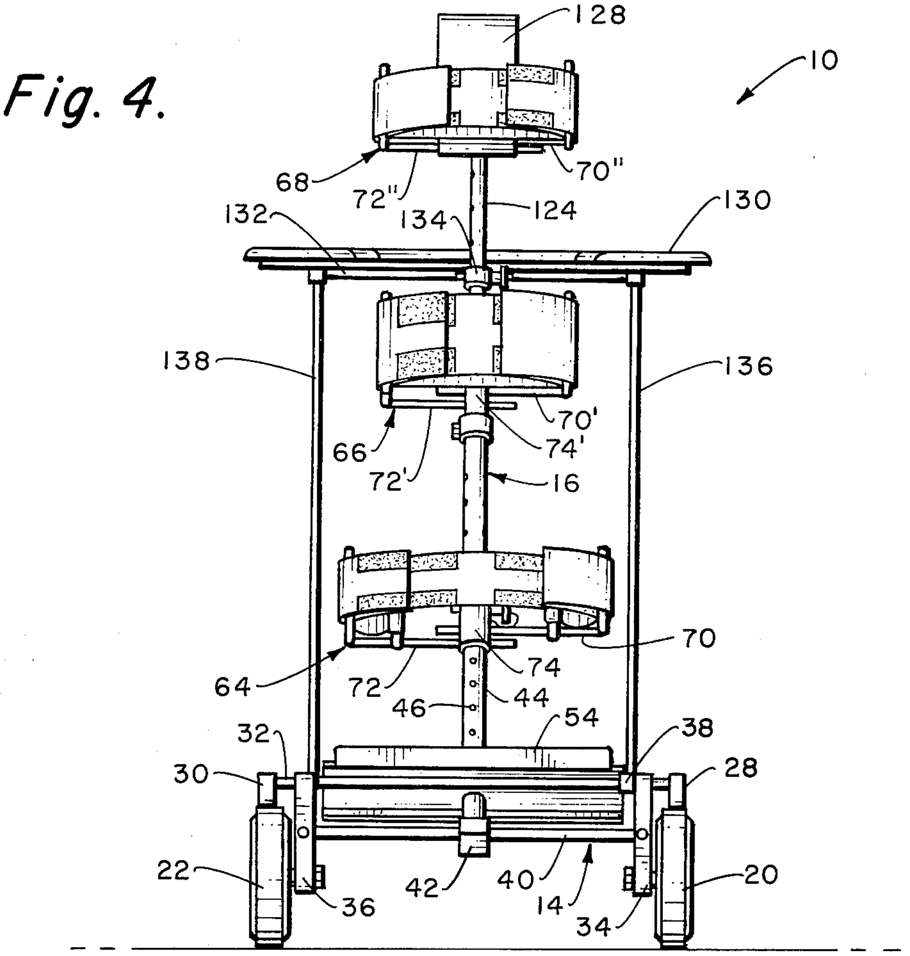
FIG. 4 is a back view of the prone stander of this invention taken along line 4—4 of FIG. 2.
Figure 7:
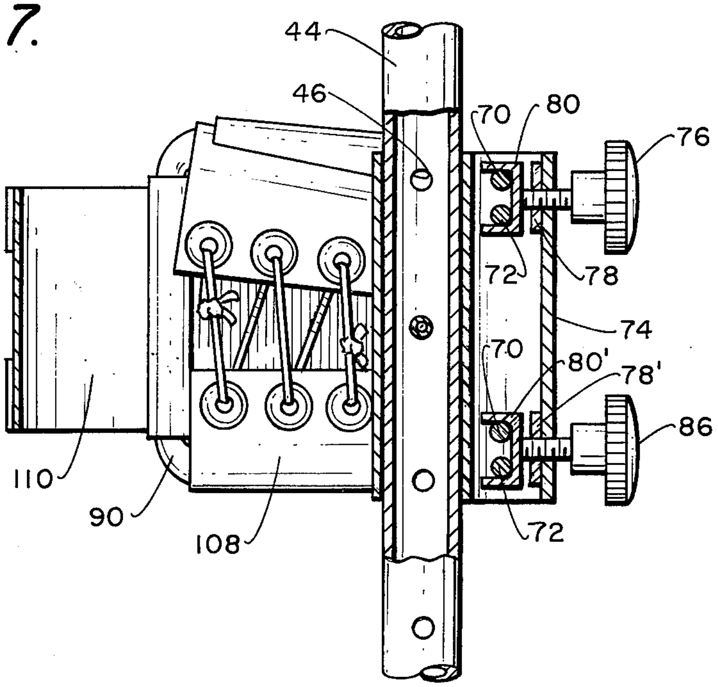
FIG. 7 is a cross-sectional view taken along line 7—7 of FIG. 6.

Fixedly secured to the rod 32 is a lever 38. The lever 38 is capable of rotating the rod one hundred and eighty degrees or between a braking position and a completely non-braking position. The non-braking position is shown in FIG. 3 with the braking position being shown in FIG. 2. With the device in the braking position, the brake members 28 and 30 are in firm contact with their respective wheels preventing movement of the prone stander. With the device in the non-braking position, the braking members 28 and 30 are spaced from the wheels 20 and 22 thereby permitting movement of the prone stander.

Pivotally mounted with respect to the main frame member 18 is a rod or bar 40. Rod 40 extends through an appropriate opening formed within a block 42. Also secured to the block 42 is a upstanding center post 44, which is the main member of the center post assembly 16. The center post 44 is a cylindrical shaped rod which is hollow and has in its outer wall thereof a plurality of holes 46.

At approximately the mid point of the length of the center post 44 is pivotally connected thereto a first brake member 48. A second brake member 50 is pivotally mounted upon the main frame member 18. The first brake member 48 telescopes within the second brake member 50. Within each of the brake members 48 and 50 are a plurality of spaced apart holes. A pair of holes for the brake member 48 may be aligned with a pair of holes within the brake member 50 and a key 52 inserted therethrough. This will lock together the brake members 48 and 50. This adjustment of the brake members 48 and 50 is for the purpose of varying the inclination of the center post 44 with respect to the base assembly 14. The reason for this inclination is that a child may not be able to completely stand at the very beginning of the rehabilitation procedure and therefore, by varying the inclination of the center post 44, the child can assume a semi-horizontal position.

Mounted on the center post 44 and included within the base assembly 14 is a supporting plate 54. The child's feet are to be placed upon the supporting plate 54. The supporting plate 54 includes an opening located within the center thereof and attached to the upper surface of the supporting plate 54 directly above the opening is connecting bracket 56. The connecting bracket 56 is basically bifurcated with the center post 44 extending between the spaced apart legs of the bracket 56. Within each of the spaced apart legs of the bracket 56 are holes 58 and 60. A locking pin 62 is to cooperate with the openings 58 and 60 and extend through one of the openings 46 located in the center post 44. The supporting plate 54 is capable of being adjusted to different positions on the center post 44 and be fixed thereby by means of the pin 62. The lowermost position of adjustment of the plate 54 is shown in FIG. 2, with the uppermost position of adjustment shown in FIG. 3. In this manner, the prone stander of this invention is capable of accommodating a wide variety of sizes of heights of children.

Attached also to the center post 44 are a plurality of supports, such as knee support 64, hip support 66 and chest support 68. The knee support 64 is composed of a pair of substantially U-shaped rod members 70 and 72, the ends of which are slidably supported in a block 74. These members 70 and 72 are laterally adjustable with respect to the block 74 in order to accommodate different sizes of children in the area of the knees. The U-shaped section of the member 70 is to be located on the outer side of the child's right knee with the U-shaped section of the member 72 being located on the outer side of the child's left knee. Once the desired lateral position has been achieved, the threaded fastener 76, which extends through an opening in the block 74 and cooperates with a nut 78 is then tightened which exerts pressure against a plate 80. Plate 80 connects with the upper legs of the members 70 and 72 and thereupon by tightening fastener 76 tightly secures these legs to the block 74. The block 74 includes an opening 82 through which is telescopingly passed the post 44. A locking pin 84 connects with the block 74 and functions to secure such to the post 44 by cooperating with one of the openings 46.

Contacting the lower legs of members 70 and 72 is a plate 80′ which is identical to plate 80. Fastener 86 operates through nut 78′ to press against plate 80′.

A similar fastener 86 connects with the block 74 and there is a similar arrangement of parts to the fastener 76 and functions to bind together the lower legs of the members 70 and 72.

Slidably mounted on the upper and lower legs of the member 70 is a member 88. A similar member 90 is slidably mounted on the upper and lower legs of member 72. The member 88 is securable in position upon the member 70 by means of set screws, such as set screw 92. The members 88 and 90 are to be adjusted to be located against the inward side of the child's knees. Therefore, the child's knees are to be located within compartments 94 and 96 and the members 70 and 72 prevent outward movement of the knees with the members 88 and 90 preventing inward movement of the knees. In this way, the child's knees are totally laterally supported.

The forward restraint for the child's knees within the compartments 94 and 96 is provided within compartment 94 by means of a wide vinyl-nylon fabric strap 98. The strap 98 is fastened together at its free ends thereof by means of hook and eye fastening assembly 100. The precise length for the particular child's knee is adjusted prior to placing a child within the prone stander so that the child's knees will not come into contact with any of the metal parts.

The same arrangement is true within compartment 96 for strap 102 which includes the use of end fastening means 104.

In order to further minimize the possiblity of the child's knees coming into contact with metal parts, the member 88 has a pad 106 of resilient material attached thereon. A similar such pad 108 is placed on member 90.

A similar fabric strap 110 is attached between the members 70 and 72 to provide the necessary restraint at the back of the child's knees. The strap 110 includes similar hook and eye fastening means for the ends of the strap, such fastening means being numbered 112 and 114.

The strap 110 is connected through the apexes of the U-shaped members 70 and 72. The ends of the strap 100 are attached to the apex of the member 88 and also to a separate bar 116 which is mounted adjacent the apex of the member 70. A similar such bar 118 is provided within the member 72 for attachment to one end of strap 102 with the other end of the strap 102 being connected to the apex of the member 90.

The construction of the hip support 66 is basically identical to the construction of the knee support 64 with the major exception being that the hip support 66 is directly fixed to the post 44. In other words, there is no telescoping adjusting movement as is provided by the knee support 64 upon the post 44. Another exception within the hip support 66 is that there is no need for any inward lateral support as is necessary with the knees. Therefore, there are no members equivalent of the members 88 and 90. Similar numerals have been employed to refer to similar parts within the hip support 66. Another distinction for the hip support 66 is that there is a forward restraint strap 120 and a back restraint strap 122 (which is similar to strap 110). It is to be noted that the strap 122 is mounted on the apex sections of the members 70' and 72' with the strap 120 being mounted on rods 124 and 126 which are formed as part of members 70' and 72', respectively and located adjacent their apexes thereof. A lock pin 84' connects with the block 74' in the same manner as lock pin 84 connects with block 74. However, since the block 74' is not movable with respect to the post 44 but is attached thereto, the purpose of the lock pin 84' is to connect with post 124. The post 124 is telescopingly received within the post 44. Attached to the upper end of the post 124 is the chest support 68. Therefore, the chest support 68 is to be adjusted in respect to the hip support 66.

The chest support 68 is again basically identical to the construction of the hip support 66 with like numerals being referred to like parts. Also, the chest support 68 includes the forward restraint strap 120' and the backward restraint strap 122' in the same manner as straps 120 and 122 of the hip support 66. It is to be understood that by using both of the straps 120 and 122 and 120' and 122' that the torso of the child's body is securely held within the device so that no portion of the body contacts any metal parts and that the child is tightly, but comfortably restrained.

Attached to the block 74' is a chin protector plate 126. This chin protector plate 126 has on its outer surface thereof a layer 128 of resilient material, such as rubber or the like. The purpose of the plate 126 and its pad 128 is that if the child's head falls that it will not contact the upper end of the block 74'', but will first contact the pad 128 and be protected against injury.

A tray 130 having an enlarged flat surface is attached at its back end thereof to a bar 132. The bar 132 is, in turn, pivotally connected to ring 134. The ring 134 is telescopingly mounted upon the post 124. A lock pin, similar to lock pin 84, is to be connectible to the ring 134 and will function to secure the back end of the tray 130 to the center post assembly 16. Positioning of the tray 130 will be accomplished after the positioning of the chest support 68'. The positioning of the tray 130 is so that the tray 130 will be substantially horizontal.

Adjacent the forward end of the tray 130 there is pivotally mounted a pair of braces 136 and 138. The braces 136 and 138 connected with the main frame member 18. At the lower end of each of the braces 136 and 138 are located a series of apertures and again a lock pin, similar to lock pin 84, are to connect with each brace 136 and 138 to the frame member 18. Due to the series of openings within the lower end of each brace member 136 and 138, the forward end of the tray 130 can also be adjusted vertically. This adjustment procedure is provided so that the tray 130 can always be located at substantially a horizontal position.

The construction of each of the lock pins, such as lock pin 84, is basically of an elongated center body of small balls 140 which are normally biased in an outward direction by a biasing means (not shown). With the lock pin 84 installed in the normal position, the balls 140 are biased outwardly and prevent accidental withdrawal of the lock pin. In order to effect release of the lock pin, the operator must push inwardly upon button 142 at the forward end of the lock pin in order to release the biasing action against the balls 140 and thereby withdraw the lock pin. Such a lock pin structure is deemed to be conventional and are commercially available. It is to be noted that each lock pin is also attached to a wire 144 which will prevent the lock pin from becoming disassociated from its intended area of usage.

The operation of the device of this invention is believed to be self-evident from the foregoing description and the child is merely placed within the device after it has been initially adjusted for the height of the child and then once the child is placed within the device it is finally adjusted in order to fit the child's specific dimensions. The child is then free to use his arms and hands and perform tasks or other movements upon the upper surface of the tray 130.

What is claimed is:

1. A prone stander comprising:

a base assembly adapted to rest upon a planar supporting surface;

a center post assembly mounted upon said base and extending upwardly therefrom;

a brace assembly interconnecting said center post assembly and said base assembly, said brace assembly to maintain an established position of said center post assembly upon said base assembly;

at least three in number of supports mounted upon said center post assemblies with there being a knee support and a hip support and a chest support, said chest and knee supports being separately longitudinally adjustable upon said center post assembly and fixable in a selected position, each of said supports including lateral adjustment means for providing lateral separate adjustment of each said support in respect to said center post assembly, each said support having an outer side wall structure for providing lateral support for the user in the outerward direction; and strap means connected to each said support for securing the user in position within said support.

2. The prone stander as defined in claim 1 wherein: said base assembly including a supporting plate upon which are to be placed the user's feet, said supporting plate being longitudinally adjustably mounted upon said center post assembly.

3. The prone stander as defined in claim 1 wherein: said center post assembly including a transverse bar member attached to one end thereof, said transverse bar being pivotally mounted upon said base assembly whereby said center post assembly is pivotable with respect to said base assembly.

4. The prone stander as defined in claim 1 wherein: said brace assembly being formed of a pair of members adjustably interconnected together.

5. The prone stander as defined in claim 1 wherein: each of said supports being constructed at rod members which are formed into a U-shaped configuration.

6. The prone stander as defined in claim 1 wherein: said knee support comprises a pair of units with there being one of said units for each of the user's knees, each of said units include a pair of members with there being an outer member and an inner member, said inner member being movably mounted upon said outer member, whereby the inner member is to be located on the inward side of the user's knee in order to prevent adduction.

7. The prone stander as defined in claim 1 wherein: said strap means comprises at least two separate strap members for each said support.

8. The prone stander as defined in claim 1 including: a tray attached to said center post assembly, a pair of elongated braces interconnecting the tray and said base assembly to maintain said tray substantially in a horizontal position.

9. The prone stander as defined in claim 8 wherein: the longitudinal center axes of said elongated braces being parallel to the longitudinal center axis of said center post assembly.

10. The prone stander as defined in claim 2 wherein: said center post assembly including a transverse bar member attached to one end thereof, said transverse bar being pivotally mounted upon said base assembly whereby said center post asembly is pivotable with respect to said base assembly.

11. The prone stander as defined in claim 10 wherein:

said brace assembly being formed of a pair of members adjustably interconnected together.

12. The prone stander as defined in claim 11 wherein:

each of said supports being constructed of rod members which are formed into a U-shaped configuraion.

13. The prone stander as defined in claim 12 wherein:

said knee support comprises a pair of units with there being one of said units for each of the user's knees, each of said units include a pair of members with there being an outer member and an inner member, said inner member being movably mounted upon said outer member, whereby the inner member is to be located on the inward side of the user's knee in order to prevent adducation.

14. The prone stander as defined in claim 13 wherein:

said strap means comprises at least two separate strap members for each said support.

15. The prone stander as defined in claim 14 wherein:

a tray attached to said center post assembly, a pair of elongated braces interconnecting the tray and said base assembly to maintain said tray substantially in a horizontal position.

* * * * *